United States Patent [19]

Chibata et al.

[11] Patent Number: 4,526,867
[45] Date of Patent: Jul. 2, 1985

[54] PROCESS FOR PREPARING IMMOBILIZED MICROORGANISM

[75] Inventors: Ichiro Chibata, Suita; Tetsuya Tosa, Nishi; Satoru Takamatsu, Yamada-Nishi, all of Japan

[73] Assignee: Tanabe Seiyaku Co., Ltd., Osaka, Japan

[21] Appl. No.: 471,850

[22] Filed: Mar. 3, 1983

[30] Foreign Application Priority Data

Mar. 19, 1982 [JP] Japan ................................. 57-45457

[51] Int. Cl.³ ....................... C12N 11/10; C12N 11/12
[52] U.S. Cl. ..................................... 435/178; 435/179
[58] Field of Search ................................ 435/178, 179

[56] References Cited

U.S. PATENT DOCUMENTS 4,138,292 2/1979 Chibata et al. ...................... 435/178
4,355,105 10/1982 Lantero .................................. 435/94

OTHER PUBLICATIONS

Birnbaum et al.–Chem. Abst., vol. 95, (1981), p. 130, 963p.

Primary Examiner—Sam Rosen
Attorney, Agent, or Firm—Birch, Stewart, Kolasch & Birch

[57] ABSTRACT

A process for preparing an immobilized microorganism which comprises cultivating a microorganism in a culture broth, treating the broth with glutaraldehyde when cultivation being completed, collecting microbial cells from the broth, admixing the microbial cells with an aqueous solution of a polysaccharide having 10 w/w % or more of sulfate moiety in the molecule thereof and then gelling the polysaccharide in the resulting mixture to entrap the microbial cells within the gel matrix of the polysaccharide. The process is suitable for the industrial preparation of immobilized microorganisms.

16 Claims, No Drawings

PROCESS FOR PREPARING IMMOBILIZED MICROORGANISM

The present invention relates to a novel process for preparing an immobilized microorganism.

Immobilized microorganims (i.e. microorganisms bound to carriers) have become of great importance in various enzymatic reactions and various processes for preparing immobilized microorganisms have been known in the prior art. For example, U.S. Pat. No. 4,138,292 discloses a process for preparing an immobilized microorganism wherein microbial cells are admixed with an aqueous solution of a polysaccharide having 10 w/w % or more of sulfate moiety in the molecule thereof, such as carrageenan, and then, the polysaccharide in the resulting mixture is gelled to entrap the microbial cells within the gel matrix thereof to obtain the immobilized microorganism. Further, the above U.S. patent also discloses the stabilization of enzymatic activity of the immobilized microorganism wherein the immobilized preparation obtained by the above process is treated with glutaraldehyde.

However, this stabilization of enzymatic activity of the immobilized microorganism by effecting the glutaraldehyde-treatment after the gel-entrapment of microbial cells is not necessarily satisfied, when it is carried out in an industrial scale. That is, since the above polysaccharide gel is relatively fragile against shear force, shape retention of the gel is liable to be impaired during the glutaraldehyde-treatment and it is difficult to uniformly effect the treatment.

In order to eliminate these difficulties, the present inventors have intensively studied the subject. As a result, it has been found that an immobilized microorganism having high enzymatic activity as well as high stability can be readily prepared by treating a culture broth of a microorganism with glutaraldehyde when cultivation thereof being completed instead of effecting the glutaraldehyde-treatment after the gel-entrapment with the polysaccharide.

The main object of the present invention is to provide a novel process for preparing an immobilized microorganism having higher enzymatic activity and higher stability which can produce the immobilized preparation without the above difficulties on an industrial scale. This object as well as other objects and advantages of the present invention will become apparent to those skilled in the art from the following description.

According to the present invention, there is provided a process for preparing an immobilized microorganism which comprises cultivating a microorganism in a culture broth, treating the broth with glutaraldehyde when cultivation is completed, collecting microbial cells from the broth, admixing the microbial cells with an aqueous solution of a polysaccharide having 10 w/w % or more of sulfate moiety in the molecule thereof, and then, gelling the polysaccharide in the resulting mixture to entrap the microbial cells within the gel matrix of the polysaccharide.

In the present invention, any microorganism having desired enzymatic activities can be used. Preferred examples of such microorganisms include *Escherichia coli* ATCC 11303 (IAM 1268) having aspartase activity, *Pseudomonas dacunhae* IAM 1152 having L-aspartate β-decarboxylase activity and the like.

As the culture broth, there can be used conventional broth suitable for cultivation of microorganisms such as the above and it can contain appropriate amounts of conventional ingredients such as carbon sources, nitrogen sources, organic nutrients, inorganic materials and the like.

Examples of the polysaccharide having 10 w/w % or more of sulfate moiety in the molecule thereof used in the present invention include carrageenan, furcellaran, cellulose sulfate and the like. Carrageenan is a polysaccharide having 20 to 30 w/w % of sulfate moiety which is obtained by refining an extract from sea weeds of Rhodophyceae such as Gigartinaceae and Solievianceae. In the present invention, commercially available carrageenan, for example, "GENU GEL WG", "GENU GEL CWG" and "GENU VISCO" (these are trade names of carrageenan manufactured by Kopenhagen Pectin Factory Ltd.) can be used. Furcellaran is a polysaccharide having 12 to 16 w/w % of sulfate moiety which is obtained by extracting one kind of sea weeds of Rhodophyceae, i.e. *Furcellaria fastigiota* and, for example, furcellaran manufactured by Litex Co., Denmark can be used. An example of cellulose sulfate is "KELCO SCS" manufactured by Kelco Co.

In carrying out the process of the present invention, firstly, the microorganism is cultivated in the culture broth. Cultivation is not limited a specific method one and it can be carried out according to a known method. Optionally, when cultivation is completed, enzymatic activity for a side reaction system of the microorganism can be removed by a known method prior to the next step of treatment with glutaraldehyde.

Then, after completion of cultivation, the culture broth is treated with glutaraldehyde. This treatment can be readily carried out by admixing glutaraldehyde with the culture broth with stirring or shaking. Preferably, the amount of glutaraldehyde to be added is such that the final concentration thereof in the culture broth is 0.1 mM to 0.5 M, particularly, 1 mM to 0.1 M. Preferably, this glutaraldehyde-treatment is carried out at 0° to 60° C., particularly, 0° to 40° C. The time required for this treatment depends upon the temperature but, usually, it is preferable to effect the treatment for 1 minute to 24 hours, particularly, 5 minutes to 5 hours. After treatment with glutaraldehyde, microbial cells are collected, for example, by centrifugation of the culture broth.

The microbial cells thus obtained are admixed with an aqueous solution of the polysaccharide having 10 w/w % or more of sulfate moiety in the molecule thereof (hereinafter simply reffered to as polysaccharide). The aqueous solution of the polysaccharide can be readily prepared by admixing the polysaccharide with water at 30° to 100° C. The concentration of the polysaccharide in the solution is, preferably, 0.2 to 20 w/w %, particularly, 1 to 10 w/w %. The aqueous solution of the polysaccharide thus obtained is admixed with the above microbial cells to prepare a mixture. In preparation of the mixture, preferably, the microbial cells are suspended in water, a physiological saline solution or a suitable buffer solution (pH 3 to 10, preferably, pH 4 to 8) and then, the resulting suspension is admixed with the aqueous solution of the polysaccharide warmed to 30° to 60° C.

The next step is to gel the polysaccharide in the mixture to entrap the microbial cells within the gel matrix of the polysaccharide. The gelation of the polysaccharide can be readily carried out by cooling the mixture. For example, when the mixture is allowed to stand at about 0° to 20° C. for about 1 minute to 5 hours, the polysaccharide is gelled and, at the same time, the microbial cells are entrapped within the resulting gel matrix of the polysaccharide. The gel thus obtained can be shaped into various forms.

Besides, the above gelation can be also carried out by a method other than cooling of the mixture. For example, the gelation can be carried out by contacting the mixture with ammonium ion or a metal ion having an atomic weight of 24 or more (e.g. potassium ion, magnesium ion, calcium ion, etc.), contacting the mixture with a compound having 2 or more of basic functional groups in the molecule thereof (e.g. methylenediamine, ethylenediamine, p-phenylenediamine, etc.) or contacting the mixture with a water-miscible organic solvent (e.g. acetone, methanol, ethanol, propanol, dioxane, tetrahydrofuran, etc.).

The immobilized microorganism prepared by the process of the present invention can be used in various enzymatic reactions according to a known method.

In comparison with the process disclosed in the above U.S. Pat. No. 4,138,292 wherein the glutaraldehyde-treatment is effected after the gel-entrapment of microbial cells, the process of the present invention wherein the glutaraldehyde-treatment is effected on the culture broth at the completion of cultivation has the following advantages.

That is, since the glutaraldehyde treatment in the process of the above prior art is effected after the gel-entrapment, shape retention of the gel is liable to be impaired and it is difficult to uniformly effect the treatment. To the contrary, since the glutaraldehyde-treatment in the process of the present invention is effected on the culture broth at the completion of cultivation, the above difficulties in the process of the prior art are eliminated and the treatment can be effected uniformly by a very simple operation. Further, according to the process of the present invention, the immobilized microorganism having higher enzymatic activity than that prepared by the process of the prior art can be obtained. Furthermore, in comparison with the immobilized microorganism obtained by the process of the prior art, the immobilized microorganism obtained by the process of the present invention maintains higher enzymatic activity for longer period of time in a continuous enzymatic reaction.

Therefore, the process of the present invention is an excellent industrial process for preparing immobilized microorganims.

The following examples and experiments further illustrate the present invention in detail but are not to be construed to limit the scope thereof.

EXAMPLE 1

Each 100 ml portions of a culture broth (pH 7.0) containing corn steep liquor (2.0%), meast (2%), fumaric acid (1.14%), diammonium fumarate (0.5%), potassium dihydrogen phosphate (0.2%) and magnesium sulfate (0.05%) were distributed in ten 500 ml Sakaguchi flasks. *Escherichia coli* ATCC 11303 (IAM 1268) was inoculated into each flask. The flask was incubated with shaking at 30° C. for 16 hours and then cooled to 5° C. to complete cultivation. 25% Aqueous solution of glutaraldehyde (2 ml) was added to the flask so that the final concentration of glutaraldehyde was 5 mM and the flask was shaken for 30 minutes. Microbial cells (23 g, wet weight) of *Escherichia coli* ATCC 11303 were collected by centrifugation of the culture broth.

Separately, GENU GEL WG (carrageenan manufactured by Kopenhagen Pectin Factory Ltd., 6 g) was dissolved in warm water (129 ml) at 45° C. to prepare an aqueous solution of carrageenan.

A suspension of the above microbial cells (23 g) in a physiological saline solution (23 ml) was admixed with the carrageenan solution at 40° C. and the resulting mixture was allowed to stand at 4° C. for 30 minutes to gel carrageenan. The resulting gel was shaped in a cubic form having about 3 mm sides. The gel was dipped in a substrate solution (400 ml) containing 1 M diammonium fumarate, allowed to stand at 37° C. for 48 hours, and then, washed with 2% aqueous solution of potassium chloride to obtain an immobilized *Escherichia coli* preparation (180 g, wet weight). The immobilized preparation thus obtained had aspartase activity of 48,680 $\mu$moles/hr/g cells.

EXAMPLE 2

Each 120 ml portions of a culture broth (pH 7.3) containing sodium glutamate (3.2%), meast (0.5%), potassium dihydrogen phosphate (0.05%) and magnesium sulfate (0.01%) were distributed in ten 500 ml Sakaguchi flasks. *Pseudomonas dacunhae* IAM 1152 was inoculated into each flask. The flask was incubated with shaking at 30° C. for 24 hours. After completion of cultivation, acetic acid (26 ml) was added to the flask to adjust to pH 4.75 and the flask was allowed to stand at 30° C. for 1 hour. 3 N Sodium hydroxide (86 ml) was added to the flask to adjust to pH 6.0 and the flask was cooled to 10° C. 25% Aqueous solution of glutaraldehyde (2.6 ml) was added to the flask so that the final concentration of glutaraldehyde was 5 mM and the flask was shaken for 30 minutes. Microbial cells (20 g, wet weight) of *Pseudomonas dacunhae* IAM 1152 were collected by centrifugation of the culture broth.

Separately, GENU GEL WG (carrageenan manufactured by Kopenhagen Pectin Factory Ltd., 4.03 g) was dissolved in warm water (85 ml) at 50° C. to prepare an aqueous solution of carrageenan.

A suspension of the above microbial cells (20 g) in a physiological saline solution (20 ml) was admixed with the carrageenan solution at 45° C. and the resulting mixture was allowed to stand at 4° C. for 30 minutes to gel carrageenan. The resulting gel was shaped in a cubic form having about 3 mm sides. The gel was washed with 2% aqueous solution of potassium chloride to obtain an immobilized *Pseudomonas dacunhae* IAM 1152 preparation (130 g, wet weight). The immobilized preparation thus obtained had L-aspartate $\beta$-decarboxylase activity of 9,050 $\mu$moles/hr/g cells.

EXPERIMENT 1

Several runs of the following continuous enzymatic reaction were carried out by using the immobilized preparation of *Escherichia coli* having aspartase activity prepared in Example 1 (the immobilized microorganism of the present invention, hereinafter referred to as Preparation A), an immobilized *Escherichia coli* preparation obtained without any glutaraldehyde-treatment (a control immobilized microorganism, hereinafter referred to as Preparation B) and an immobilized *Escherichia coli* preparation obtained by effecting glutaraldehyde-treatment after gel-entrapment of microbial cells (a control immobilized microorganism, hereinafter referred to as Preparation C) to example stability of enzymatic activity and productivity of L-aspartic acid of each preparation.

Preparations B and C used as the controls were prepared as follows:

Preparation B

This preparation was prepared by the same manner as described in Example 1 except that the treatment of glutaraldehyde was not effected.

Preparation C

This preparation was prepared by suspending the above Preparation B (10 g, wet weight) in 2% aqueous solution of potassium chloride (100 ml) containing 5 mM glutaraldehyde, shaking the suspension at 5° C. for 15 minutes and then washing with 2% aqueous solution of potassium chloride.

Continuous Enzymatic Reaction

Each immobilized *Escherichia coli* preparation (4 g) was packed in a jacketed column (1.6 cm in diamter and 10.5 cm in length) and 1 M aqueous solution of ammonium fumarate containing $10^{-3}$ M magnesium chloride (pH of the solution was adjusted to 8.5 by ammonia) was continuously passed through the column at 37° C. at a flow rate of 40 ml/hr. The eluate from the column was collected at intervals and the half-life of aspartase activity (days required for the enzymatic activity to be reduced to 50% of the initial activity) and L-aspartic acid productivity of the immobilized preparation were determined by measuring the amount of L-aspartic acid in the eluate. The quantitative measurement of L-aspartic acid was conducted by a bioassay using *Leuconostoc mesenteroides* P-60.

Results

The results are shown in Table 1. As is seen from Table 1, Preparation A (the immobilized microorgnism of the present invention) maintains higher enzymatic activity and has excellent L-aspartic acid productivity in comparison with Preparations B and C.

TABLE 1

| Continuous operation period (days) | Aspartase activity (μmoles L-aspartic acid/hr/g cells) | | |
|---|---|---|---|
| | Preparation A | Preparation B | Preparation C |
| 1 | 48,680 | 56,340 | 37,460 |
| 10 | 48,000 | 51,100 | 36,400 |
| 20 | 47,360 | 46,030 | 35,410 |
| 30 | 45,100 | 41,860 | 34,260 |
| 40 | 43,880 | 37,900 | 33,290 |
| 50 | 42,730 | 34,450 | 32,480 |
| 80 | 38,910 | 25,530 | 29,710 |
| 100 | 36,700 | 20,910 | 28,110 |
| 150 | 32,830 | 12,760 | 23,900 |
| 200 | 27,940 | 7,730 | 21,070 |
| 250 | 24,300 | 4,750 | 18,120 |
| Half-life of aspartase activity (days) | 250 | 70 | 240 |
| L-Aspartic acid* productivity | 309 | 100 | 228 |

*L-Aspartic acid productivity is expressed as the relative value of the total amount of L-aspartic acid produced within the half-life period of the enzymatic activity by taking the amount obtained by using Preparation B as 100.

EXPERIMENT 2

Several runs of the following continuous enzymatic reaction were carried out by using the immobilized preparation of *Pseudomonas dacunhae* IAM 1152 having L-aspartate β-decarboxylase activity (the immobilized microorganism of the present invention, hereinafter referred to as Preparation D), an immobilized *Pseudomonas dacunhae* IAM 1152 preparation obtained without any glutaraldehyde-treatment (a control immobilized microorganim, hereinafter referred to as Preparation E) and an immobilized *Pseudomonas dacunhae* IAM 1152 preparation obtained by effecting glutaraldehyde-treatment after gel-entrapment of microbial cells (a control immobilized microorganism, hereinafter referred to as Preparation F) to examine stability of enzymatic activity and L-alanine productivity of each preparation.

Preparations E and F used as the controls were prepared as follows:

Preparation E

This preparation was prepared by the same manner as described in Example 2 except that the treatment of glutaraldehyde was not effected.

Preparation F

This preparation was prepared by adding 0.2 M phosphate buffer solution (pH 7, 20 ml) containing 1.67 M L-lysine hydrochloride to the above Preparation E (10 g, wet weight), allowing the resulting mixture to stand at 10° C. for 10 minutes, adding thereto 25% aqueous solution of glutaraldehyde (13.3 ml), allowing the mixture to stand at 10° C. for 10 minutes and then washing with 2% aqueous solution of potassium chloride.

Continuous Enzymatic Reaction

Each immobilized *Pseudomonas dacunhae* IAM 1152 preparation (4 g) was packed in a jacketed column (1.6 cm in diamter and 10.5 cm in length) and 1 M aqueous solution of ammonium L-aspartate containing $10^{-4}$ M pyridoxal phosphate (pH of the solution was adjusted to 5.5 by ammonia) was continuously passed through the column at 37° C. at a flow rate of 18 ml/hr. The eluate from the column was collected at intervals and the half-life of L-aspartate β-decarboxylase activity (days) and L-alanine productivity of the immobilized preparation were determined by measuring the amount of L-alanine in the eluate. The quantitative measurement of L-alanine was conducted by a bioassay using *Leuconostoc citrovorum* ATCC 8081.

Results

The results are shown in Table 2. As is seen from Table 2, Preparation D (the immobilized microorganism of the present invention) maintains higher enzymatic activity and has excellent L-alanine productivity in comparison with Preparations E and F.

TABLE 2

| Continuous operation period (days) | L-Aspartate β-decarboxylase activity (μmoles L-alanine/hr/g cells) | | |
|---|---|---|---|
| | Preparation D | Preparation E | Preparation F |
| 1 | 9,050 | 9,050 | 4,680 |
| 10 | 8,910 | 5,520 | 4,550 |
| 20 | 8,320 | 3,330 | 4,400 |
| 30 | 8,000 | 2,080 | 4,240 |
| 40 | 7,530 | 1,210 | 4,120 |
| 50 | 6,910 | 750 | 4,110 |
| 70 | 7,530 | 280 | 3,750 |
| 100 | 6,910 | — | 3,390 |
| 150 | 6,090 | — | 2,910 |
| 200 | 5,350 | — | 2,470 |
| 250 | 4,610 | — | 2,190 |
| 300 | 4,140 | — | 1,860 |
| 350 | 3,650 | — | 1,600 |
| Half-life of L-aspartate β-decarboxylase | 270 | 14 | 225 |

TABLE 2-continued

| Continuous operation | L-Aspartate β-decarboxylase activity (μmoles L-alanine/hr/g cells) | | |
|---|---|---|---|
| period (days) | Preparation D | Preparation E | Preparation F |
| activity (days) L-Alanine productivity* | 1,929 | 100 | 831 |

*L-Alanine productivity is expressed as the relative value of the total amount of L-alanine produced within the half-life period of the enzymatic activity by taking the amount obtained by using Preparation E as 100.

What is claimed is:

1. A process for preparing an immobilized microorganism which comprises cultivating a microorganism in a culture broth, treating the broth with glutaraldehyde when cultivation is completed, collecting microbial cells from the broth, admixing the microbial cells with an aqueous solution of a polysaccharide having 10 w/w % or more of sulfate moiety in the molecule thereof and then gelling the polysaccharide in the resulting mixture to entrap the microbial cells within the gel matrix of the polysaccharide.

2. A process according to claim 1, wherein the microorganism is *Escherichia coli* having aspartase activity or *Pseudomonas dacunhae* having L-aspartate $\beta$-decarboxylase.

3. A process according to claim 1, wherein the polysaccharide is carrageenan, furcellaran or cellulose sulfate.

4. A process according to claim 1, wherein the treatment with glutaraldehyde is carried out by admixing glutaraldehyde with the broth with stirring or shaking in such an amount that the final concentration of glutaraldehyde in the broth is 0.1 mM to 0.5 M.

5. A process according to claim 1, wherein the aqueous solution of the polysaccharide contains 0.2 to 20 w/w % of the polysaccharide.

6. A process according to claim 1, wherein the microbial cells are suspended in water, a physiological saline solution or a buffer solution of pH 3 to 10 and then the resulting suspension is admixed with the aqueous solution of the polysaccharide at 30° to 60° C.

7. The process as recited in claim 1, which further comprises removing enzymatic activity for side reaction systems of the microorganism prior to treatment with glutaraldehyde.

8. The process as recited in claim 1, wherein the treatment with glutaraldehyde is conducted at a temperature range of 0° to 60° C.

9. The process as recited in claim 1, wherein the treatment with glutaraldehyde is conducted during a time period of 1 minute to 24 hours.

10. The process as recited in claim 1, wherein the microbial cells are collected by centrifugation of the culture broth.

11. The method as recited in claim 1, wherein the aqueous solution of the polysaccharide is prepared by admixing the polysaccharide with water at a temperature of 30° to 100° C.

12. The method as recited in claim 1, wherein the polysaccharide is gelled in the mixture by cooling.

13. The method as recited in claim 1, wherein polysaccharide is gelled in the mixture by contacting the mixture with an ammonium ion, a metal ion having an atomic weight of 24 or more,
methylenediamine, ethylenediamine, p-phenylenediamine, or a water-miscible organic solvent.

14. An immobilized microorganism which is prepared by the process comprising the steps of: cultivating a microorganism in a culture broth, treating the broth with glutaraldehyde when cultivation is completed, collecting microbial cells from the broth, admixing the microbial cells with an aqueous solution of a polysaccharide having 10 w/w % or more of sulfate moiety in the molecule thereof and then gelling the polysaccharide in the resulting mixture to entrap the microbial cells within the gel matrix of the polysaccharide.

15. The immobilized microorganism according to claim 14, wherein the microorganism is *Escherichia coli* having aspartase activity or *Pseudomonas dacunhae* having L-aspartate $\beta$-decarboxylase.

16. The immobilized microorganism according to claim 14, wherein the polysaccharide is carrageenan, furcellaran or cellulose sulfate.

* * * * *